United States Patent [19]

King

[11] Patent Number: 4,568,328
[45] Date of Patent: Feb. 4, 1986

[54] AUTOMATED PHOTOPHORESIS BLOOD PORTION CONTROL METHODS AND APPARATUS

[75] Inventor: Martin J. King, Largo, Fla.

[73] Assignee: Extracorporeal Medical Specialties, Inc., King of Prussia, Pa.

[21] Appl. No.: 665,832

[22] Filed: Oct. 29, 1984

[51] Int. Cl.$^4$ ............................................. A61F 2/16
[52] U.S. Cl. ..................................................... 604/6
[58] Field of Search ................................. 604/4, 5, 6

[56] References Cited

U.S. PATENT DOCUMENTS

| | | | |
|---|---|---|---|
| 4,321,919 | 3/1982 | Edelson | 604/6 |
| 4,401,431 | 8/1983 | Arp | 604/4 |
| 4,447,191 | 5/1984 | Bilstad et al. | 604/6 X |
| 4,481,827 | 11/1984 | Bilstad et al. | 604/6 X |

*Primary Examiner*—Harland S. Skogquist
*Attorney, Agent, or Firm*—Mark A. Hofer

[57] ABSTRACT

Automated control methods and apparatus are provided for the separation and collection of desired blood portions for use in an extracorporeal photophoresis treatment system wherein a photoactivatable agent, in contact with leukocyte enriched blood from a patient is irradiated and then returned to said patient.

3 Claims, 3 Drawing Figures

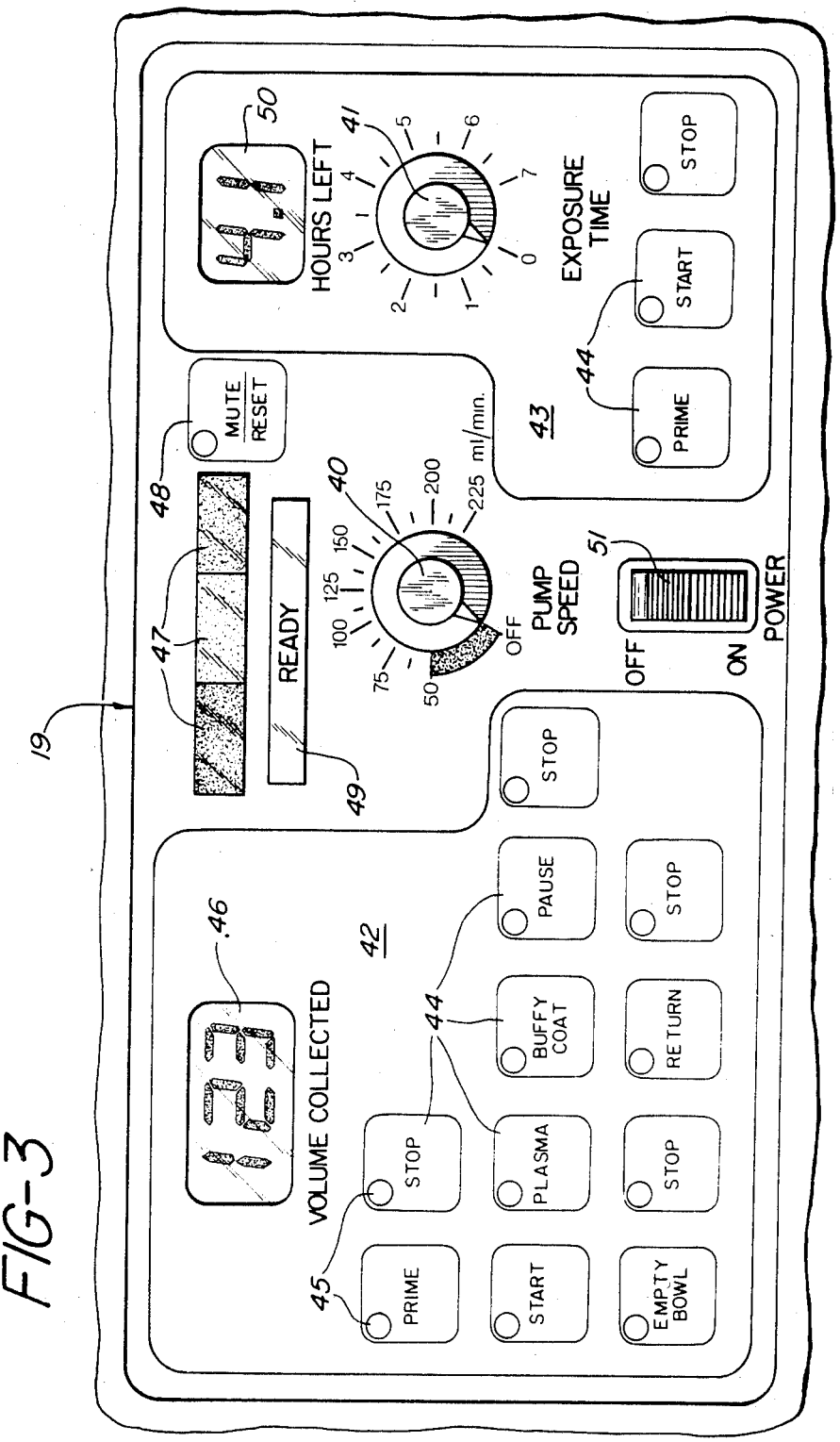

4,568,328

AUTOMATED PHOTOPHORESIS BLOOD PORTION CONTROL METHODS AND APPARATUS

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems required solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602, of Taylor describes a preferred form of a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8T5/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to the aforesaid Taylor application, the relevant aspects of which are fully incorporated herein by reference.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another object of the present invention to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another object of the present invention to provide a suitably automated instrument which can be monitored and operated by less trained personnel thereby lowering treatment costs in accordance with the recently enacted fiscal policies.

It is yet still another object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparant upon study of the accompanying drawings wherein:

FIG. 3 shows the control panel for the system.

SUMMARY OF THE INVENTION

In accordance with the principles and objects of the present invention there are provided methods for automated blood portion control, and related apparatus, for use in extracorporeally photoactivating a photoactivatable reagent in contact with blood cells. The overall patient treatment procedure comprises the steps of collecting and separating on a continuous basis blood from a patient while the patient is connected to the patient treatment apparatus, returning undesired blood portions obtained during separation, and disconnecting the patient from the treatment system while the desired portion is photoactivatably treated whereupon the thusly treated cells are returned to the patient. Thus, the patient treatment system maximizes a patient's safety and procedurally optimizes the various aspects of such photoactivation treatment by breaking the entire procedure down into three phases or modes. The apparatus, in the first mode, collects and separates blood on a continuous basis as it is withdrawn from the patient and returns unwanted blood portions to the patient all steps of which are accomplished while the patient is connected to the apparatus. Thereafter, prior to energizing the irradiation sources for photoactivating the photoactivatable reagent in contact with the desired blood portion, the patient is disconnected from the machine thereby isolating him (or her) physically and electrically from the energizing high voltage, a potential source of harm. Following photoactivation, the treated cells may then be facilely returned to the patient utilizing a variety of techniques, the preferred being a simple drip chamber gravity feed infusion line.

Figure 1:
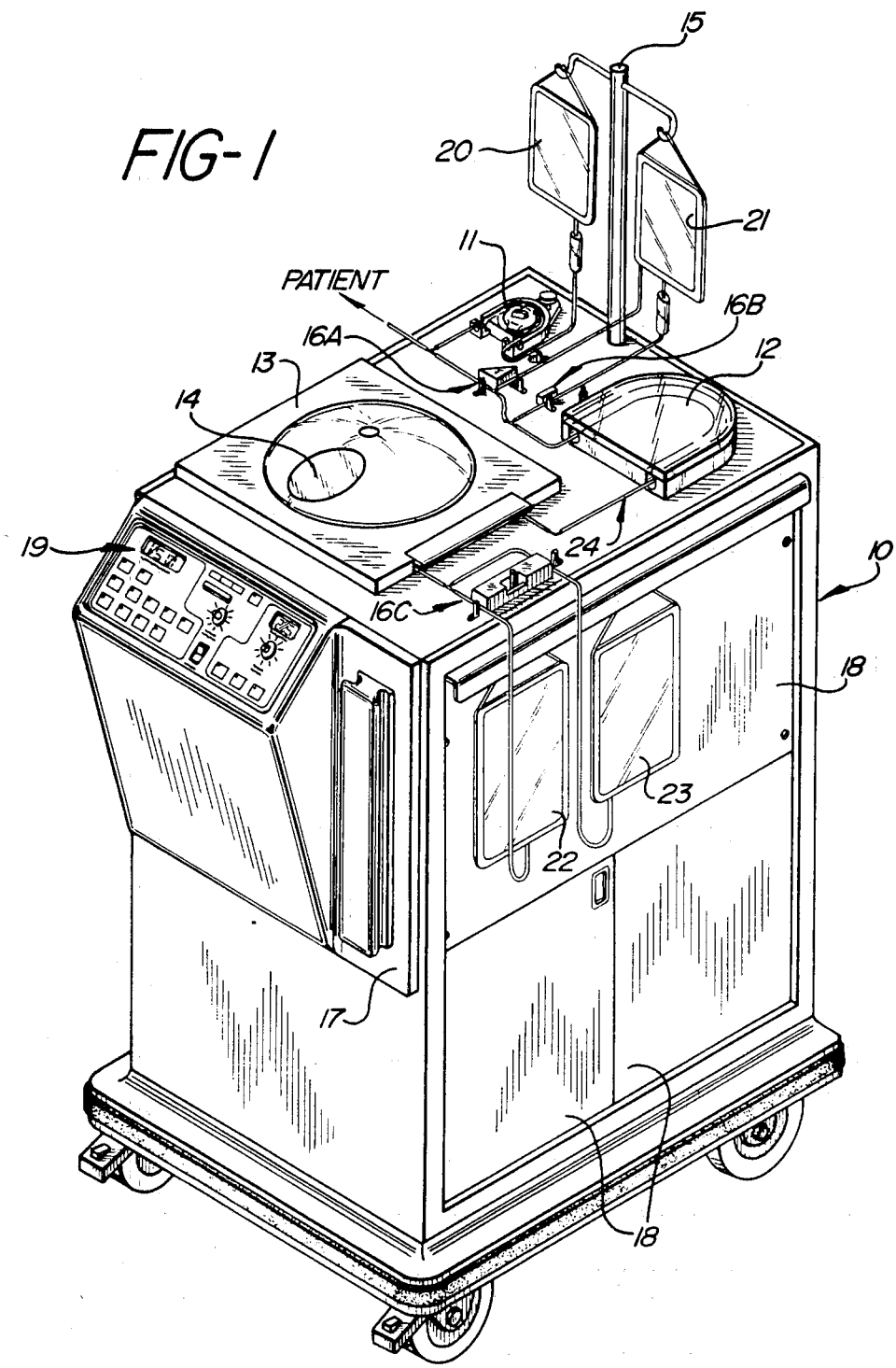
FIG. 1 illustrates a preferred configuration of the system in the collection and separation mode.
Figure 2:
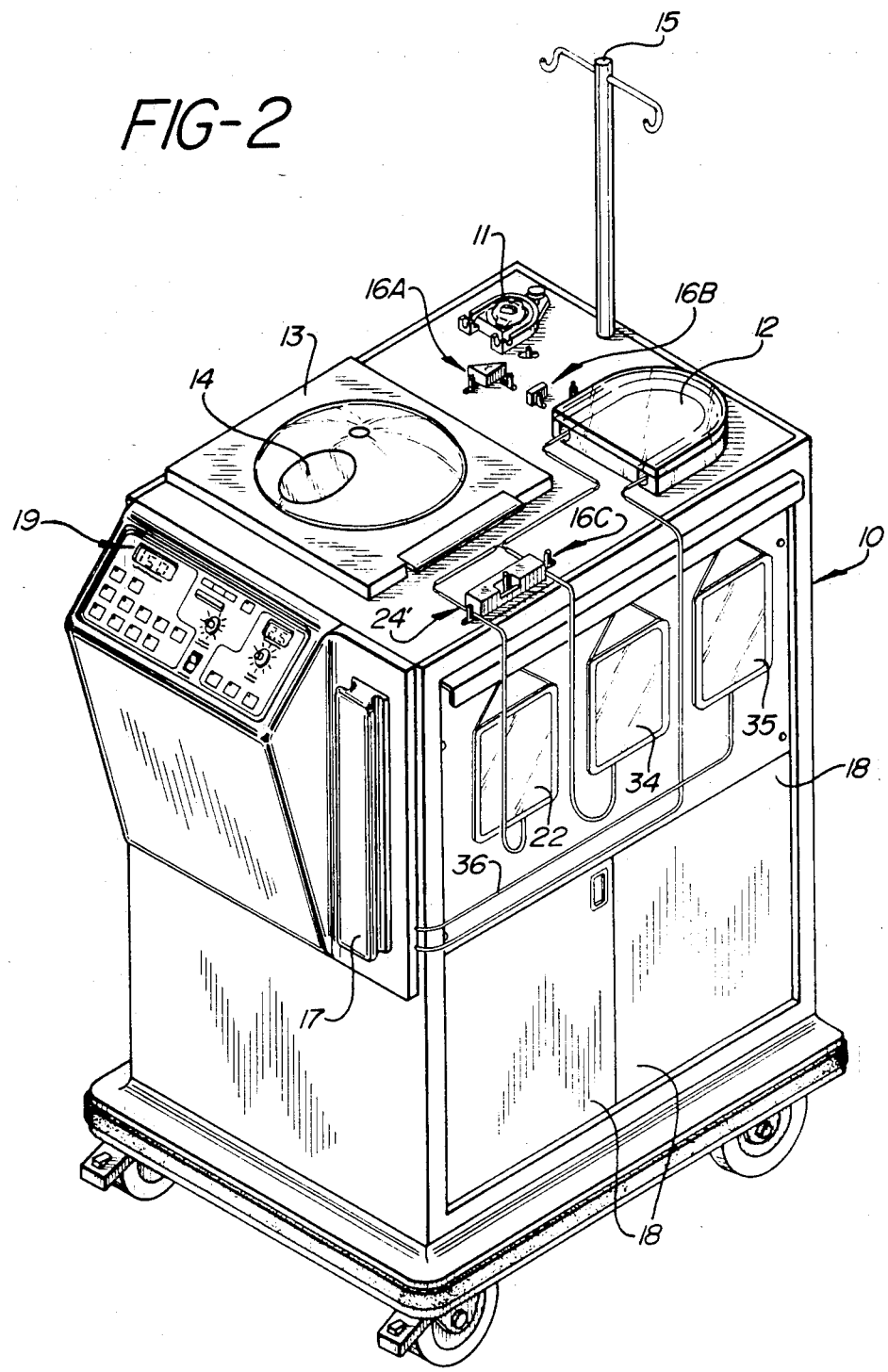
FIG. 2 depicts the system in the treatment mode.

FIGS. 1, 2, and 3 show various aspects of the apparatus developed by the assignee hereof for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 to Goss entitled "Three Phase Irradiation Treatment Process"; U.S. Ser. No. 665,831 to King entitled "Electronic Control Methods for Puvapheresis Apparatus"; U.S. Ser. No. 665,827 to Troutner entitled "Valve Apparatus for Photoactivation Patient Treatment System"; U.S. Ser. No. 665,833 to King et al. entitled "Patient Photopheresis Treatment Apparatus and Method"; and U.S. Ser. No. 665,817 to Troutner entitled "Cassette Drawer Assembly for Photoactivation Patient Treatment System", the relevant parts of which are incorporated herein by reference.

The operation of the device and performance of the methods can be divided into three basic phases or modes, depicted in part by FIGS. 1 and 2. The first phase is shown substantially in FIG. 1 wherein the patient is connected at the point shown such as by venipuncture methods well-known and developed to a high degree in the dialysis arts. Patient blood, as it flows to the apparatus 10 (alternately referred to herein as the puvapheresis apparatus or system) is preferably infused, under control of pump 11, with an anti-coagulant agent contained in container 20 hung from stand 15. Control of the flow of patient blood to the remainder of apparatus 10 is controlled largely by clamping means 16a which has the dual function of also controlling flow in the reverse direction as well as flow to return container 21; clamp 16a acting as an "or" valve. Normally the blood flows through tubing 24 through blood pump 12 into a continuous centrifuge 13. This continuous centrifuge, available commercially from suppliers such as Dideco and others, is preferably capable of continuously separating blood based on the differing densities of the individual blood components. "Continuously", as used herein means that; as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through magnifying observation point port 14 of the centrifuge cover, can detect qualitatively when the centrifuge emits plasma (as opposed to priming solution), leukocyte enriched portions and non-leukocyte enriched portions such as erythrocytes. Based on the operator's observations, he or she enters through control panel 19 (specifically via panel portion 42) the identification of the individual blood portions as they are emitted from the centrifuge. Based on this information entered by keys 44 (e.g. PLASMA, BUFFY COAT or leukocyte enriched portion) on control panel 19, (shown in FIG. 3) the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry and the contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the erythrocyte enriched portion which is pumped into return bag 21 is gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, line 24 may be expected to contain sterilized air which is preferably removed by suitable priming operations utilizing the anti-coagulation agent in container 20; both the air and the priming solution being collected in container 23.

Also to be noted is the predetermination of the desired leukocyte enriched volume and plasma volume to be collected within container 22 as well as the number of cycles to be employed to collect same. These volumes are selected largely in accorance with the individual volume capacities of the containers as well as the treatment cassette to be described later. Accordingly, these volumes are set in order to preferably optimize handling efficiency and to ensure patient safety. For instance, one preferred selection would be as follows: 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions and the procedure in general. Alternately, more cycles will also permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is required with respect to these data inputs.

Referring now to FIG. 2, a second tubing set or mode of the apparatus 10 is shown showing the leukocyte enriched container 22 connected via tubing line 24' through valve 16c, blood pump 12 to the treatment cassette behind door 17 with a return line 36 to reservoir container 35. The tubing set for the second mode will also preferably include container 34 for providing a priming solution for evacuating air contained within tubing set 24' and the cassette treatment module described in copending application of Taylor, U.S. Ser. No. 650,602. In brief summary, the Taylor cassette comprises a plurality of ganged cylindrical cavities each of which is concentrically mounted around a cylindrical irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the first step, PRIME, may be initiated whereupon the priming solution from container 34 is pumped via blood pump 12 through tubing set 24' and the treatment cassette emptying into reservoir 35. Thereafter, the operator, by pushing START in section 43, initiates actual photoirradiation treatment whereupon the leukocyte enriched portion of the blood collected within container 22 is pumped through tubing set 24' in accordance with suitably altered valve 16c through blood pump 12 to the treatment cassette and returning 36 to reservoir 35.

The treatment cassette container assembly 17 further comprises bubble detectors connected to the central control means for detecting the presence of air about to enter the treatment cassette. The presence of the air indicates the complete evacuation of container 22 and signals the end of the first treatment pass. Thereafter, the central control means reverses the direction of blood pump 12 which draws blood from container 35 back through the treatment cassette through the blood pump and to container 22. The actual direction of the blood flow through the treatment cassette is of no significance as flow in either direction is equally photoactivated. An advantage gained by reversing direction (as opposed to constant cycling in the same direction) is the hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then reversal thereof is continued until the desired exposure time is attained. At that point, the treated blood portion is then preferably returned to blood container 22 and the tubing set 24' discarded. Container 22 is then ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, are present. To further decrease the risk of contamination to the patient blood and blood portions, each time a connection is made or broken, it is preferably only done once. Thus, container 22 would have three connection ports; one for the first mode collection of the leukocyte enriched blood portion, one for the second mode treatment phase shown by FIG. 2, and the third for the third operational mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included in the central section are lights 47 and 49. Alphanumeric display 49 indicates alarms and status regarding the machine's sequential operations. Status lights 47 are preferably provided in green, yellow, and red colors in order to provide at a glance the overall operating status of apparatus 10. Further included is a mute reset button 48 for quieting an audible alarm activated in the event an alarm condition occurs and operator input is required.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

The aforedescribed photopheresis blood treatment apparatus is made largely possible by the instant invention which specifically provides an automated control method for directing the blood portions derived from the continuous centrifuge into particular containers.

The automated method performs in accordance with preset volume determinations which are manually entered pursuant to a physician's direction. These predetermined volumes specify the total volume to be contained within container 22 by setting forth the volume of plasma and the volume of leukocyte enriched blood portion to be collected and directed thereto. Additionally included within these condition setting parameters is preferably the ability to set forth the number of cycles of blood collection and separation required or desired in order to obtain the desired blood volumes.

The actual volumes collected are determined in accordance with the blood volume pumped by the blood pump. This may be suitably monitored and communicated to the central control means by specifically monitoring the speed of the blood pump rotation. Shaft rotation may be conveniently monitored such as by attachment of a slotted disk to the shaft and passage of the slots determined by an optical sensor. The resultant periodic signal may be conveniently correlated with speed of rotation by circuit designs well-known in the art. The rotational speed coupled with the known volume pumping characteristics of the pump, e.g. mls/rotation, will provide the necessary information to permit accurate calculation of the volume of blood pumped.

In actual operation, the ideal procedure would be as follows. The operator primes the tubing set, the blood pump, and the centrifuge with the anti-coagulation solution contained in container 20 via the PRIME button. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 23. At some point, the priming solution will be completely displaced from the rotating centrifuge and plasma will begin to emerge. This emergence may be directly observed through port 14 whereupon the operator presses the PLASMA key on control panel section 42. Thereafter, the central control means automatically directs the plasma into container 22 keeping track of the volume as it does so on the basis that the volume being pumped into the continuous centrifuge must equal the volume emerging therefrom. This continues until the operator indicates the leukocyte enriched portion, i.e. buffy coat has begun by pressing the BUFFY COAT entry key whereupon, the leukocyte enriched portion continues to container 22, however, the volume so directed is monitored as buffy coat volume. Alternately, if all of the predetermined plasma volume is collected prior to the emergence of the buffy coat, then the central control means automatically diverts, by valve 16c, the emerging plasma fluid stream to container 23. In that instance, upon the emergence of the buffy coat and the keying of the BUFFY COAT data entry switch 44, the central control means diverts the emerging buffy coat into container 22 again keeping track of its volume.

The collection of the buffy coat will ideally continue in accordance with both the predetermined buffy coat volume as well as the number of collection/separation cycles, also a predetermined condition by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and container 23 and returning the predominantly erythrocytes and perhaps excess plasma to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the instant invention serves to automatically keep track of the volumes as they are collected thereby facilitating the institution of a convenient number of cycles whereby the removal of large blood volumes from the patient is avoided. Not only is patient safety enhanced thereby, but the automated nature of the procedure eliminates numerous potential sources of error since, in accordance with programming supplied to the central control means, the operator need not attempt to keep track of various plasma and leukocyte enriched volumes collected while still being assured that the final solution for treatment will contain the desired leukocyte concentration based on the predetermined conditions of plasma volume and buffy coat volume.

What is claimed is:

1. In an extracorporeal photophoresis leukocyte enriched blood treatment system for photoactivating a reagent, a control method for obtaining said leukocyte enriched blood from whole blood from a patient comprising the steps of:

pumping, said whole blood from said patient into a continuous centrifuge having capacity limits whereby leukocytes are substantially separated from erythrocytes on the basis of differing densities, said continuous centrifuge adapted to continuously receive whole blood and to discharge plasma and leukocyte enriched blood as whole blood is received until the capacity limit has been attained;

monitoring the volume of blood pumped and electronically communicating said volume to central control means for controlling said treatment system;

directing plasma, derived from said centrifuge, to a first container in response to a first manual instruction and monitoring the volume of plasma so directed by means of the volume pumped into said continuous centrifuge;

further directing in response to a second manual instruction, said leukocyte rich portion emerging from said centrifuge into said first container and monitoring separately the volume so directed by means of the volume pumped into said continuous centrifuge; and directing excess plasma and nonleukocyte enriched fluids to a second container;

wherein said directing steps are controlled by said central control means so that predetermined volumes of plasma and leukocyte enriched portions are collected in said first container, excess volumes thereover being automatically directed by said central control means to said second container whereby a predetermined leukocyte enriched blood portion mixed with plasma is obtained from said patient's whole blood, said leukocyte enriched plasma mixture being suitable for photoactivation and said excess plasma, if any, and said nonleukocyte enriched fluids in said second container being suitable for reinfusion to the patient.

2. The control method of claim 1 further comprising the steps of returning the contents of the second container to the patient and then repeating the steps of claim 1 for a predetermined number of cycles, said central control means collecting said plasma and leukocyte enriched portions from each cycle into said first container in accordance with said predetermined volume and cycle conditions.

3. In an extracorporeal treatment system for photoactivating a reagent, apparatus for obtaining a plasma and leukocyte enriched blood portions, from whole blood from a patient, suitable for photoactivation comprising:

blood pump means having known volume pumping characteristics electronically coupled to central control means;

continuous centrifuge means for receiving and separating on the basis of density whole blood into plasma enriched, leukocyte enriched portions and nonleukocyte enriched portions, and for discharging said portions as whole blood is received;

a first container for receiving said plasma and said leukocyte enriched blood portion;

a second container for receiving fluids not directed to said first container;

a tubing set for communicating blood from said patient to said treatment system and communicating with said blood pump means, said centrifuge, and said first and second containers; and valve means for directing flow from said centrifuge to said first or second containers in response to electronic signals from said central control means wherein said central control means is adapted to receive information regarding the desired plasma and leukocyte enriched blood portion volumes to be contained in said first container and, in response to manually entered identification of the particular blood portion being discharged from said centrifuge and said desired blood volume information, said control means in cooperation with said valve means causes the desired plasma volume and leukocyte enriched blood volume to be collected in said first container and other fluids to be collected in said second container.

* * * * *